United States Patent [19]

Drews et al.

[11] Patent Number: 4,912,357

[45] Date of Patent: Mar. 27, 1990

[54] ULTRASONIC MHZ OSCILLATOR, IN PARTICULAR FOR LIQUID ATOMIZATION

[75] Inventors: Wolf-Dietrich Drews, Lichtenfels; Klaus Van der Linden, Kronach, both of Fed. Rep. of Germany

[73] Assignee: Siemens Aktiengesellschaft, Berlin and Munich, Fed. Rep. of Germany

[21] Appl. No.: 248,314

[22] Filed: Sep. 19, 1988

Related U.S. Application Data

[63] Continuation of Ser. No. 49,129, May 12, 1987, abandoned.

[30] Foreign Application Priority Data

May 20, 1986 [DE] Fed. Rep. of Germany ....... 3616713

[51] Int. Cl.$^4$ .............................................. H01L 41/08
[52] U.S. Cl. .................................... 310/323; 310/325; 310/335; 239/102.2
[58] Field of Search ........................... 36/321–323, 36/325, 328; 239/102.1, 102.2; 134/1

[56] References Cited

U.S. PATENT DOCUMENTS

| 3,214,101 | 10/1965 | Perron | 310/325 X |
| 3,292,910 | 12/1966 | Martner | 310/323 X |
| 3,357,641 | 12/1967 | Martner | 310/323 X |
| 3,421,939 | 1/1969 | Jacke | 310/325 X |
| 4,153,201 | 5/1979 | Berger et al. | 310/325 X |
| 4,301,968 | 11/1981 | Berger et al. | 239/102.2 |
| 4,474,326 | 10/1984 | Takahashi | 239/102.2 |
| 4,540,123 | 9/1985 | Junger et al. | 239/102.2 |
| 4,541,564 | 9/1985 | Berger et al. | 239/102.2 |

FOREIGN PATENT DOCUMENTS

| 1425897 | 2/1969 | Fed. Rep. of Germany . |
| 2032433 | 12/1972 | Fed. Rep. of Germany . |
| 2557958 | 6/1977 | Fed. Rep. of Germany . |
| 2029159 | 3/1980 | United Kingdom ................ 310/323 |

Primary Examiner—Mark O. Budd
Attorney, Agent, or Firm—Kenyon & Kenyon

[57] ABSTRACT

An ultrasonic MHz oscillator, in particular for liquid atomization, where at the upper, widening end of the upwardly decreasingly tapering amplitude transformer fastened on a planar piezoceramic disk, a continuously concave surface adapted to the liquid quantity and liquid surface tension is disposed comprising a concave mirror. The mirror cavity is adapted to receive the liquid to be atomized. With the oscillator, smallest droplets can be produced without coupling liquid, so that the oscillators find use above all in pocket inhalators.

10 Claims, 1 Drawing Sheet

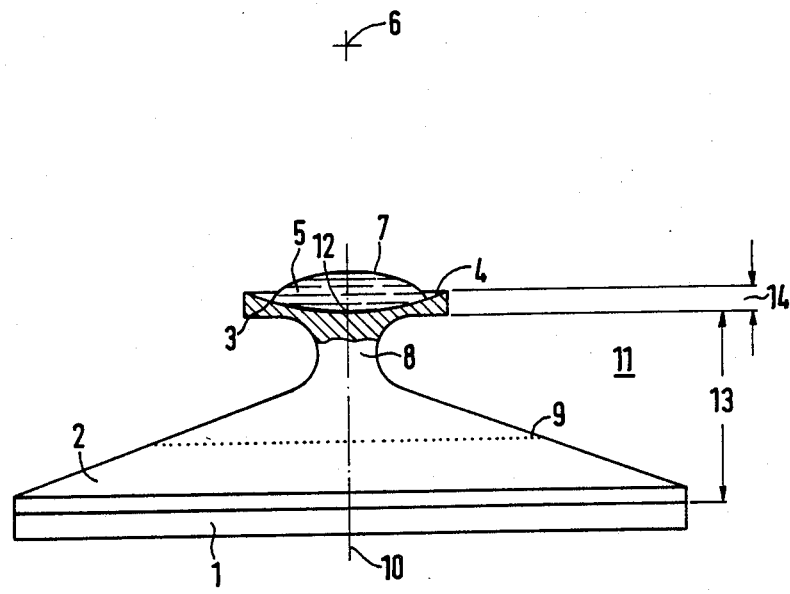

ULTRASONIC MHZ OSCILLATOR, IN PARTICULAR FOR LIQUID ATOMIZATION

This application is a continuation, of application Ser. No. 049,129, filed 5/12/87 now abandoned.

BACKGROUND OF THE INVENTION

The present invention relates to an ultrasonic oscillator, in particular for megahertz operation, and in particular further for liquid atomization.

From U.S. Pat. No. 3,904,896 and U.S. Pat. No. 3,738,574 a piezoelectric oscillatory system, in particular for liquid atomization, is known, with a stimulating oscillator consisting of a bending oscillator plate with transducer plate, the bending oscillator plate being coupled with a thinner working plate by means of a web. Alternatively, the bending oscillator plate and the web may be formed as a truncated cone, merging one into the other, and being in one piece with the working plate. Such oscillatory systems can be used for the atomization of liquids in kHz ultrasonic atomizers. A disadvantage of the known MHz atomizers is that the diameters of the droplets produced are substantially larger. Thus, usually less than 50% of the produced aerosol matter is inhalable. Inhalable aerosol is obtained here only with mechanical separation systems.

Known also is atomization by means of a hemispherical oscillator oscillating in the MHz range. Thereby an aerosol of different diameter, namely of about 0.1 micron to several millimeters, is obtained. The particles of larger diameter must be retained by means of a mechanical droplet separator.

SUMMARY OF THE INVENTION

It is therefore an object of the present invention to atomize minute liquid volumes ($V \leqq 15$ ul) in the MHz range (1 MHz$\leqq f \leqq$5 MHz) without a mechanical droplet filter at lowest electrical excitation power ($P \leqq 30$ W) and without coupling via liquid media, to droplets of about less than 40 microns. It is to be possible to atomize a quantity of liquid proportioned onto an ultrasonic atomizer at once, independent of position, within a minimum of time.

The above and other objects of the invention are achieved by an ultrasonic MHz oscillator, in particular for the atomization of liquids, comprising a piezoceramic, a metal amplitude transformer having a concavely curved plate, said transformer comprising an upwardly tapering amplitude transformer which comprises at an upper widening end a continuous concave surface adapted to the liquid quantity and liquid surface tension, said concave surface comprising a concave mirror for receiving the defined liquid quantity to be atomized, and, at a lower end, said piezoceramic comprising a planar piezoceramic disk.

The concave mirror fastened at the upper end of the amplitude transformer receives in its cavity the liquid to be atomized. The concave mirror makes it possible to bring the supplied liquid quantity to the point best suitable for the atomization. The camber of the concave mirror is adapted to the liquid quantity and surface tension of the liquid which through their properties and shape are suitable for cavitation nucleus formation. The dimensions of the concave mirror are chosen so that the liquid quantity to be atomized is received well and the liquid to be atomized does not drip off even under various inclined positions of the ultrasonic atomizer.

The chosen geometry permits an equally good efficient operation also when pouring with silicone rubber.

In ultrasonic atomizers according to the invention, the piezoceramic—in contrast to the known ultrasonic atomizers operating in the MHz range in thickness direction—operates without counter-mass and without coupling to a liquid volume. The small droplet diameters needed for example for inhalation therapy are produced without mechanical separation of the large drops. Mechanical droplet selection is necessary in the MHz atomizers known at present.

With the invention it is possible, at smallest liquid volume $v \leqq 15$ ul in a range of 1 MHz$\leqq f \leqq$5 MHz, lowest electrical excitation power ($P \leqq 30$ W), to atomize 50% of the liquid volume to be atomized, to droplets of less than 40 microns. The majority of the droplets has a diameter of less than 5 microns. A mechanical drop filter is not required. The invention permits without coupling via liquid media within a very short time $t \leqq 3$ sec, at a liquid quantity proportioned into the concave mirror all at once, a position-independent atomization of minute liquid volumes.

As the piezoceramic are suitable the known piezoelectric materials, in particular lead-zirconate-titanate.

The material of the amplitude transformer consists preferably of cavitation- and corrosian-resistant CrNi steel. The concave mirror consists preferably of CrNi steel, in particular of the same material as the amplitude transformer, or else of metal powder-filled plastics.

The total height of the amplitude transformer should be, including the thickness of the concave mirror, a multiple, preferably 4 to 6 times the half wavelength in the amplitude transformer.

The thickness of the concave mirror preferably corresponds to one half wavelength in ultrasound, but may be from ¼ to 1.5 wavelength.

The diameter of the concave mirror should be preferably a multiple, preferably 3 to 7 times the diameter of the neck.

The diameter of the neck is preferably 1 to 3 times the wavelength of the ultrasound in the amplitude transformer.

Oscillators according to the invention can generally be used for atomizing liquids. To special advantage they are used for atomizing medications and aromatic substances, aqueous solutions or water. The atomization is especially advisable if droplet sizes to a maximum of 50 microns are needed which are to be inhalable. For use in inhalators, battery operation independent of power supply is to be stressed, also the possible small structural form of the apparatus.

BRIEF DESCRIPTION OF THE DRAWING

The invention will be described in greater detail in the following detailed description with reference to the single drawing FIGURE which shows an atomizer according to the invention in a side view.

DETAILED DESCRIPTION

In the atomizer 11, a piezoceramic disk 1 is glued on at the amplitude transformer 2 of CrNi steel. By 9 is designated the neutral zone of the atomizer cone, in which mechanical damping does not become apparent by impedance variation. On the upper part of the amplitude transformer 2, tapering to a neck 8, a concave mirror 3 of V2A (stainless) steel is applied. In the cavity 4 is the liquid 5 to be atomized, for example, bronchospasmalytics. The surface of the liquid to be atomized is denoted by 7, 10 denotes the axis of symmetry, 12 denotes the intersection of the axis of symmetry 10 with the concave mirror 3, and 6 denotes the focus. Reference numeral 13 marks the total height of the amplitude transformer. The thickness of the concave mirror at the outer edge thereof preferably corresponds to one half wavelength of the ultrasound, but may be from ¼ to 1.5 times the wavelength. The thickness is shown by reference numeral 14 in the drawing figure.

An ultrasonic atomizer of the geometry according to the invention poured into silicone rubber, shows equally good efficient operation as in the state not poured in. It can be poured in from the piezoceramic 1 to maximally the neck height 8. Further there is no problem in clamping the oscillator or mechanically fixing the ultrasonic atomizer under an O-ring which is fitted in the neutral zone 9 of the transformer.

In the foregoing specification, the invention has been described with reference to a specific exemplary embodiment thereof. It will, however, be evident that various modifications and changes may be made thereunto without departing from the broader spirit and scope of the invention as set forth in the appended claims. The specification and drawings is, accordingly, to be regarded in an illustrative rather than in a restrictive sense.

What is claimed is:

1. An ultrasonic MHz oscillator for operation in the range from approximately 1 MHz to 5 MHz and operating in a power range of $\leq 30$ watts, for the atomization of a dosed amount of liquid into an aerosol spray inhalable into the human lung, comprising a piezoceramic, a metal amplitude transformer having a concavely curved plate, said amplitude transformer comprising an upwardly tapering amplitude transformer which comprises at an upper widening end a continuous concave surface without an opening in said surface adapted to the dosed liquid quantity to be atomized and liquid surface tension, said concave surface comprising a concave mirror for receiving the dosed liquid quantity to be atomized, and further comprising at a lower end, said piezoceramic comprising a planar piezoceramic disk, said piezoceramic disk being operated without a counter-mass on a side of said piezoceramic disk opposite said amplitude transformer, the total height of the ultrasonic atomizer being 4 to 6 times the half wavelength of the amplitude transformer and the total height of the amplitude transformer to the diameter of the piezoceramic being in the ratio of 1:2.

2. An ultrasonic MHz oscillator for operation in the range from approximately 1 MHz to 5 MHz, for the atomization of liquids into an aerosol spray inhalable into the human lung, comprising a piezoceramic, a metal amplitude transformer having a concavely curved plate, said amplitude transformer comprising an upwardly tapering amplitude transformer which comprises at an upper widening end a continuous concave surface adapted to the liquid quantity to be atomized and liquid surface tension, said concave surface comprising a concave mirror for receiving the defined liquid quantity to be atomized, and further comprising at a lower end, said piezoceramic comprising a planar piezoceramic disk, said piezoceramic disk being operated without a counter-mass on a side of said piezoceramic disk opposite said amplitude transformer, the distance of a focus of the mirror from the intersection of an axis of symmetry of the oscillator with the concave mirror corresponding to double the diameter of the concave mirror.

3. An ultrasonic MHz oscillator for operation in the range from approximately 1 MHz to 5 MHz, for the atomization of liquids into an aerosol spray inhalable into the human lung, comprising a piezoceramic, a metal amplitude transformer having a concavely curved plate, said amplitude transformer comprising an upwardly tapering amplitude transformer which comprises at an upper widening end a continuous concave surface adapted to the liquid quantity to be atomized and liquid surface tension, said concave surface comprising a concave mirror for receiving the defined liquid quantity to be atomized, and further comprising at a lower end, said piezoceramic comprising a planar piezoceramic disk, said piezoceramic disk being operated without a counter-mass on a side of said piezoceramic disk opposite said amplitude transformer, the distance of a focus of the mirror from the intersection of an axis of symmetry of the oscillator with the concave mirror corresponding to the diameter of a neck portion of the transformer below the mirror.

4. The ultrasonic MHz oscillator recited in claim 1, wherein the taper of the amplitude transformer forms a neck, the diameter of which is adapted to the operating frequency of the atomizer.

5. The ultrasonic MHz oscillator recited in claim 4, wherein the operating frequency of the atomizer corresponds to the wavelength of the ultrasound in the amplitude transformer.

6. The ultrasonic MHz oscillator recited in claim 1 wherein the thickness of the concave mirror at an outer edge thereof corresponds to one half wavelength of the ultrasound in the amplitude transformer.

7. The ultrasonic MHz oscillator recited in claim 1 wherein the height of the amplitude transformer is 4 to 6 times the half wavelength in the amplitude transformer.

8. The ultrasonic MHz oscillator recited in claim 4 wherein the diameter of the concave mirror is 3.5 times the neck diameter and the neck diameter is ½ to 2 times that of the wavelength in the amplitude transformer.

9. The ultrasonic MHz oscillator recited in claim 1 wherein the thickness of the piezoceramic corresponds to the half wavelength in the ceramic.

10. An ultrasonic MHz oscillator for operation in the range from approximately 1 MHz to 5 MHz, for the atomization of liquids into an aerosol spray inhalable into the human lung, comprising a piezoceramic, a metal amplitude transformer having a concavely curved plate, said amplitude transformer comprising an upwardly tapering amplitude transformer which comprises at an upper widening end a continuous concave surface adapted to the liquid quantity to be atomized and liquid surface tension, said concave surface comprising a concave mirror for receiving the defined liquid quantity to be atomized, and further comprising at a lower end, said piezoceramic comprising a planar piezoceramic disk, said piezoceramic disk being operated without a counter-mass on a side of said piezoceramic disk opposite said amplitude transformer, the total height of the ultrasonic atomizer being 4 to 6 times the half wavelength of the amplitude transformer and the total height of the amplitude transformer to the diameter of the piezoceramic being in the ratio 1:2.

* * * * *